United States Patent [19]
Cujec et al.

[11] Patent Number: 6,159,684
[45] Date of Patent: Dec. 12, 2000

[54] HIV TRANS-ACTIVATOR TAT BINDING TO CDK7 AND ACTIVATION OF CTD PHOSPHORYLATION

[75] Inventors: Thomas P. Cujec; B. Matija Peterlin, both of San Francisco, Calif.

[73] Assignee: The Regents of the University of California, Oakland, Calif.

[21] Appl. No.: 09/420,081

[22] Filed: Oct. 18, 1999

Related U.S. Application Data

[62] Division of application No. 08/943,495, Oct. 3, 1997, Pat. No. 5,994,055.

[51] Int. Cl.⁷ .............................. C12Q 1/70; G01N 33/53; A61K 38/00
[52] U.S. Cl. .................. 435/5; 435/7.2; 530/326
[58] Field of Search .......................... 435/5, 7.2; 530/326

[56] References Cited

U.S. PATENT DOCUMENTS 5,733,920  3/1998  Mansuri et al. .................. 514/337

OTHER PUBLICATIONS

Blau et al, Three Functional Classes of Transcriptional Activation Domains, *Molecular and Cellular Biology*, 16: (5) 2044–2055 (1996).

Parada et al., Enhanced processivity of RNA polymerase II triggered by Tat–induced phosphorylation of its carboxy–terminal domain, *Nature* 384:375–378 (1996).

Cujec et al., The Human Immunodeficiency Virus Transactivator Tat Interacts with the RNA Polymerase II Holoenzyme, *Mollecular and Cellular Biology*, 27: (4)1817–1823 (1977).

Feaver et al., CTD Kinase Associated with Yeast RNA Polymerase II Initiation Factor b, *Cell Press*, 67:1223–1230 (1991).

Feaver et al., Relationship of CDK–Activating Kinase and RNA Polymerase II CTD Kinase TfIIH/TFIIK, *Cell Press*, 79:1103–1109 (1994).

Rossignol et al., Sustrate specificity of the cdk–activating kinase (CAK) is altered upon association with TFIIH, *The EMBO Journal*, 16: (7)1628–1637 (1977).

Yankulov et al., Regulation of CDK7 substrate specificity by MAT1 and TFIIH, *The EMBO Journal*, 16: (7)1638–1647 (1997).

Drapkin et al., Human cyclin–dependent–kinase–activating kinase exists in three distinct complexes, *Proc. Natl. Acad. Sci.*, 93:6488–6493 (1996).

Reardon, et al., Isolation and characterization of two human transcription factor IIH (TFIIH)–related complexes: ERCC2/CAK and TFIIH, *Proc. Natl. Acad Sci.*, 93:6482–6487 (1996).

Chun et al., Requirements for RNA Polymerase II Carboxy-l–terminal Domain for Activated Transcription of Human Retroviruses Human T–Cell Lymphotropic Virus I and HIV–1, *The Journal of Biochemical Chemistry*, 271 (44)27888–27894 (1996).

(List continued on next page.)

*Primary Examiner*—Hankyel T. Park
*Attorney, Agent, or Firm*—Townsend and Townsend and Crew LLP

[57] ABSTRACT

The present invention relates to methods of inhibiting Tat trans-activation in a cell and methods of assaying for inhibitors of Tat trans-activation.

8 Claims, 1 Drawing Sheet

OTHER PUBLICATIONS

Okamoto, et al., Transactivation by human immunodeficiency virus Tat protein requires the C–terminal domain of RNA polymerase II, *Proc. Natl. Acad. Sci.*, 93: 11575–11579 (1996).

Yang, et al., The Human Immunodeficiency Virus Tat Proteins Specifically Associate with TAK in Vivo and Require the Carboxyl–Terminal Domain of RNA Polymerase II for Function, *Journal of Virology* 70(7) :4576–4584 (1996).

Fisher et al., A Novel Cyclin Associates with MO15/CDK7 to form the CDK–Activating Kinase, *Cell Press*, 78:713–714, (1994).

Ossipow et al., A Mammalian RNA Polymerase II Holoenzyme Containing All Components Required for Promoter–Specific Transcription Initiation, *Cell Press*, 83:(137–146), (1995).

Mäkelä et al., A cyclin associated with the CDK–activating kinase MO15, *Nature* 371:254–257 (1994).

Maldonado et al., A Human RNA polymerase II complex associated with SRB and DNA–repair proteins, *Nature* 381:86–89 (1996).

HIV TRANS-ACTIVATOR TAT BINDING TO CDK7 AND ACTIVATION OF CTD PHOSPHORYLATION

CROSS REFERENCE TO RELATED APPLICATIONS

This application is a divisional of and claims the benefit of U.S. Ser. No. 08/943,495, issued Oct. 3, 1997 now U.S. Pat. No. 5,994,055, herein incorporated by reference in its entirety.

FIELD OF THE INVENTION

The present invention relates to methods of inhibiting Tat trans-activation in a cell and methods of assaying for inhibitors of Tat trans-activation.

BACKGROUND OF THE INVENTION

The human immunodeficiency virus encodes a highly conserved transcriptional trans-activator Tat, which is expressed early in the viral life cycle and is essential for viral replication and progression to disease (Cullen et al., *Cell* 73:417–20 (1993); Jones et al., *Annu. Rev. Biochem.* 63:717–743 (1994)). Tat binds to the trans-activation response (TAR) RNA stem-loop located from positions +1 to +60 in the viral 5' long terminal repeat (LTR). Interactions between Tat and TAR are absolutely required for the increased processivity of RNA polymerase II (pol II) and the production of full-length viral transcripts (Kao et al., *Nature* (London) 330:489–493 (1987); Laspia et al., *Cell* 59:283–292 (1989); Marciniak et al., *EMBO J.* 10:4189–4196 (1991); Kato et al., *Genes Dev.* 6:655–666 (1992)). Tat is unique because it is the only eukaryotic transcription factor known to function via RNA (Madore et al., *Virology* 206:1150–1154 (1995)). Although the mechanism by which Tat increases transcription elongation rates is unknown, common regulatory themes must exist between viral and cellular genes since Tat can relieve pol II pausing when artificially targeted to the c-myc promoter (Wright et al., *J. Mol. Biol.* 243:568–573 (1994)).

Tat can be divided into two functional domains. The activation domain contains 48 N-terminal amino acids and interacts with the cellular transcriptional machinery. A 10 amino acid basic domain is required for the binding of Tat to TAR (Jones et al., *Annu. Rev. Biochem.* 63:717–743 (1994)). Cellular proteins are clearly required for the function of Tat (Carroll et al., *J. Virol.* 66:2000–2007 (1992); Madore et al., *J. Virol.* 67:3703–3711 (1993)). At least one protein, encoded by the human chromosome 12, is required for the efficient binding of Tat to TAR (Hart et al., *Science* 246:488–491 (1989); Alonso et al., *J. Virol.* 66:4617–4621 (1992)). Numerous other proteins have been postulated to interact with the activation domain of Tat. These include general transcription factors (GTFs) such as the core pol II (Mavarikal et al., *Proc. Natl. Acad. Sci. USA* 93:2089–2094 (1996)), the TATA box-binding protein (TBP) (Kashanchi et al., *Nature* (London) 367:295–299 (1994); Veschambre et al., *J. Mol. Biol.* 250:169–180 (1995)), the TBP-associated factor $TAF_{II55}$ (Chiang et al., *Nature* (London) 267:531–536 (1995)) and TFIIH (Blau et al., *Mol. Cell. Biol.* 16:2044–2055 (1996); Parada et al., *Nature* (London) 384:375–378 (1996)). Upstream DNA bound activators such as Sp1 have also been identified as possible co-activators of Tat (Jeang et al., *J. Virol.* 67:6224–6233 (1993)). In addition, a wide variety of other proteins that interact with Tat but whose role in transcription is somewhat unclear have also been identified (Nelbock et al., *Science* 248:1650–1653 (1990); Desai et al., *Proc. Natl. Acad. Sci. USA* 88:8875–8879 (1991); Zhou et al., *Science* 274:605–610 (1996)).

Recently, Tat has been demonstrated to interact with the pol II holoenzyme (Cujec et al., *Mol. Cell. Biol.* 17:1817–1823 (1997)). This large mega-dalton complex consists of core pol II, a subset of general transcription factors (TFIIE, TFIIF, TFIIH), human SRBs (suppressors of mutations in polymerase B), which confer the ability of the pol II holoenzyme to respond to activators, and proteins involved in chromatin remodeling (SWI/SNF) and nucleotide repair (Kim et al., *Cell* 77:599–608 (1994); Ossipow et al., *Cell* 83:137–146 (1995); Chao et al., *Nature* (London) 380:82–85 (1996); Maldonado et al., *Curr. Opin. Cell Biol.* 7:352–361 (1995); Wilson et al., *Cell* 84:235–244 (1996)). One component of the pol II holoenzyme, TFIIH, contains nine polypeptides (ERCC3, ERCC2, p62, p54, p44, CDK7 (MO15), cyclin H, MAT 1, and p34) (Drapkin et al., *Trends Biochem. Sci.* 19:504–508 (1994); Hoeijmakers et al., *Curr. Opin. Genet. Dev.* 6:26–33 (1996)).

TFIIH also contains a kinase activity that can phosphorylate the C-terminal domain (CTD) of core pol II (Feaver et al., *Cell* 67:1223–1230 (1991); Lu et al., *Nature* 358:641–645 (1992)). The kinase activity resides in the cyclin-dependent kinase 7 (CDK7) polypeptide (Feaver et al., *Cell* 79:1103–1109 (1994); Roy et al., *Cell* 79:1093–1101 (1994); Serizawa et al., *Nature* (London) 374:280–282 (1995); Shiekhattar et al., *Nature* (London) 374:283–287 (1995)). In association with cyclin H, CDK7 forms the CDK-activating kinase (CAK) complex, which phosphorylates cyclin-dependent kinases (CDKs) involved in the regulation of the cell cycle. Association of MAT 1 with the CAK dimer stabilizes the complex and allows for the activation of CAK independent of the phosphorylation of CDK7 on the threonine at position 170 (Fisher et al., *Cell* 78:713–724 (1994); Fisher et al., *Cell* 83:47–57 (1995)). Moreover, the CAK trimer is much more efficient at phosphorylating the CTD than the CAK dimer (Rossignol et al., *EMBO J.* 16:1628–1637 (1997); Yankulov et al., *EMBO J.* 16:1638–1646 (1997)). The tripartite CAK can exist in three distinct complexes in cells. The majority is present as free CAK. However, CAK can also exist as a CAK-ERCC2 complex as well as in association with the core TFIIH (ERCC3, p62, p54, p44 and p34) (Drapkin et al., *Proc. Natl. Acad. Sci. USA* 93:6488–6493 (1996); Reardon et al., *Proc. Natl. Acad. Sci. USA* 93:6482–6487 (1996)). The association of CAK with TFIIH confers kinase activity to TFIIH and renders it transcriptionally competent. Interestingly, the yeast homologue of CDK7, Kin28 is found only in a complex with TFIIH and is devoid of CAK activity (Cismowski et al., *Mol. Cell. Biol.* 15:2983–2992 (1995)). Instead, CAK activity resides in a novel protein called Civ1 or CAK1p (Kladis et al., *Cell* 86:553–564 (1996); Thuret et al., *Cell* 86:565–576 (1996)).

The eukaryotic pol II is unique among polymerases in that it contains multiple heptapeptide repeats of the sequence (YSPTSPS) at the C-terminal end of the protein, which comprise the CTD (Dahmus, *Prog. Nucleic Acid Res. Mol. Biol.* 48:143–179 (1994); Dahmus, *Biochim. Biophys. Acta.* 1261:171–182 (1995)). A large number of kinases capable of phosphorylating the CTD in vitro have been identified. However, the functional relevance of these kinases remains unclear. To date, CDK7/cyclin H (TFIIH) and CDK8/cyclin C (human homologues of the yeast SRB10/SRB11) are the major kinases associated with transcription factors that can phosphorylate the CTD (Liao et al., *Nature* (London) 374:193–196 (1995); Serizawa et al., *Nature* (London)

374:280–282 (1995); Shiekhattar et al., *Nature* (London) 374:283–287 (1995)).

Pol II enters into the assembling transcription complex with its CTD unphosphorylated (IIA form). However, the CTD of elongating polymerases is highly phosphorylated (IIO form), primarily on its serine and threonine residues (Uchiumi et al., *J Biol Chem* 265:89–95 (1990); Laybourn et al., *J. Biol. Chem.* 265:13165–13173 (1990)). This observation led to the suggestion that the phosphorylation of the CTD is important for promoter clearance and for the processivity of pol II. Numerous additional observations support this contention: 1) the CTD of polymerases paused on the Drosophila hsp 70 promoter prior to heat shock activation are hypophosphorylated (IIA) while those of actively elongating polymerases are hyperphosphorylated (IIO) (O'Brien et al., *Nature* (London) 370:75–77 (1994)), 2) inhibitors of CTD kinases inhibit promoter clearance and elongation of pol II in vitro (Yankulov et al., *J. Biol. Chem.* 270:23922–23925 (1995); Yankulov et al., *Mol. Cell. Biol.* 16:3291–3299 (1996)), 3) the kinase activity of TFIIH is required for the clearance of the DHFR promoter but not for the initiation of its transcription (Akoulitchev et al., *Nature* (London) 377:557–560 (1995)), and 4) mutations in the yeast pol II CTD, the yeast homologue of CDK7 (Kin 28), or SRB2, a subunit of the pol II holoenzyme, each inhibit the processivity of pol II in vivo (Akhtar et al., *EMBO J.* 15:4654–4664 (1996)). The identification of CTD-binding proteins with homology to serine/arginine-rich (SR) proteins suggest that the phosphorylation of the CTD might also provide a mechanism for coupling transcription and pre-mRNA processing (Yuryev et al., *Proc. Natl. Acad. Sci. USA* 93:6975–6980 (1996)).

Recently, it has been demonstrated that the CTD is absolutely required for the production of long transcripts from the HIV LTR in vitro and in vivo (Chun et al., *J. Biol. Chem.* 271:27888–27894 (1996); Okamoto et al., *Proc. Natl. Acad. Sci. USA* 93:11575–11579 (1996); Parada et al., *Nature* (London) 384:375–378 (1996); Yang et al., *J. Virol.* 70:4576–4584 (1996)). In contrast, basal transcription and the production of short transcripts from the HIV LTR is independent of the CTD. Because TFIIH kinase activity is involved with CTD phosphorylation and Tat trans-activation, there is a need to identify the specific interactions between TAT and TFIIH, in order to develop inhibitors of Tat trans-activation of HIV transcription. Such inhibitors are needed to develop HIV therapeutics.

SUMMARY OF THE INVENTION

The present invention identifies the cellular protein, CDK7, that binds to the activation domain of Tat, and demonstrates that this interaction is critical for the trans-activation of Tat. The invention therefore also provides inhibitors of Tat trans-activation, and assays for identifying inhibitors of Tat trans-activation.

In one aspect, the invention provides a method of inhibiting Tat trans-activation in a cell. This method includes the step of contacting the cell, e.g., a human cell, with an inhibitor of CDK7-catalyzed phosphorylation of CTD.

The inhibitor can be a CDK7 pseudosubstrate, e.g., a peptide. In one embodiment, the pseudosubstrate is an amino acid subsequence of the CDK2 polypeptide, and in another embodiment, the amino acid subsequence is mC2p, which is a subsequence of CDK2. The inhibitor can also act by inhibiting binding between Tat and CDK7. Therefore, in one embodiment, the inhibitor is a subsequence of Tat or CDK7.

In another aspect, the invention provides a method of screening for inhibitors of Tat trans-activation. The method includes the steps of: (a) contacting Tat; pol II, and HIV promoter sequences operably linked to a structural gene with a substance suspected of inhibiting Tat trans-activation; and (b) assaying for Tat trans-activation of the HIV promoter sequence operably linked to the structural gene.

The assay can be an in vitro run-off transcription assay or an in vivo transcription assay. The inhibitor can be a CDK7 pseudosubstrate, e.g., a peptide.

DETAILED DESCRIPTION OF THE INVENTION

I. Introduction

Figure 1:
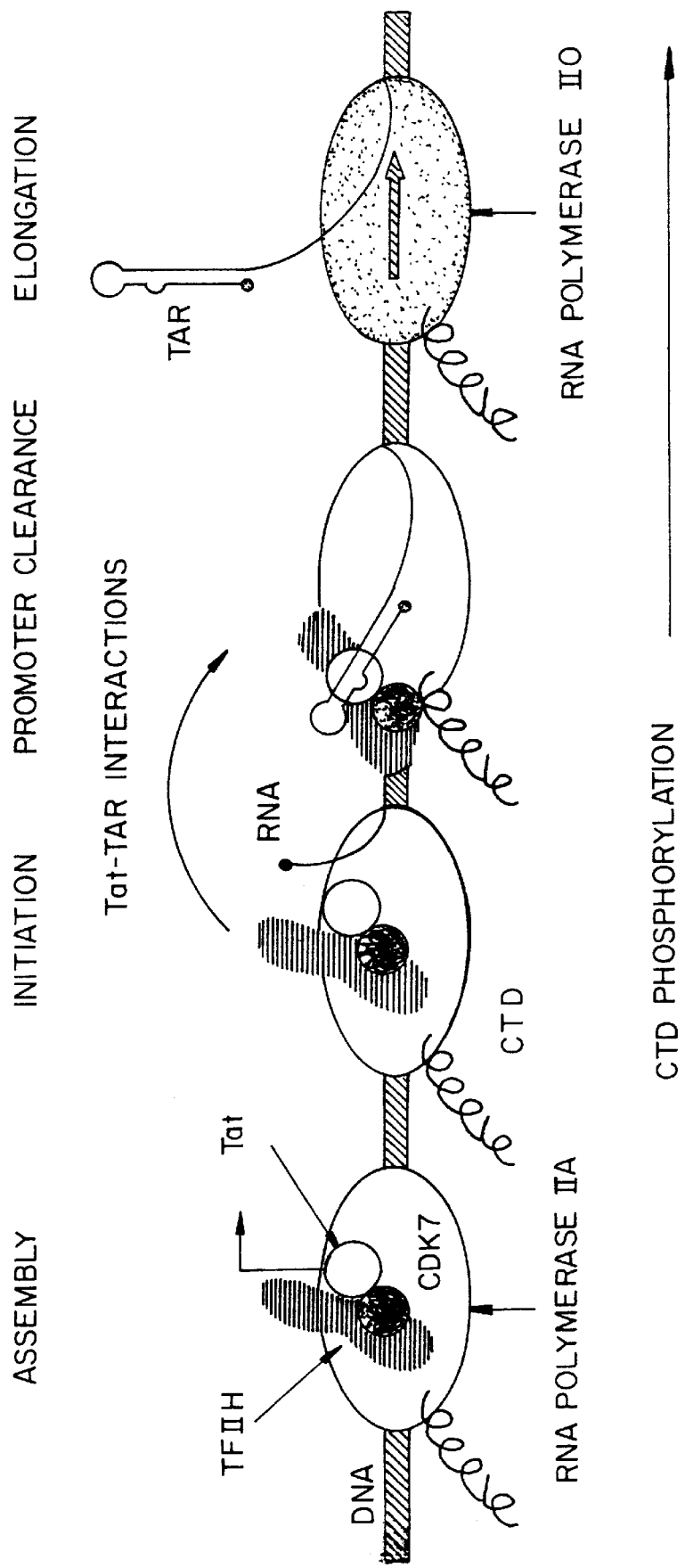
FIG. 1 shows a model of the mechanism by which Tat increases the processivity of Pol II. Tat activated transcription of the HIV promoter can be divided into four stages: (i) assembly of the transcription complex onto the DNA template, (ii) initiation of transcription, (iii) promoter clearance, and (iv) elongation of pol II along the DNA template. In this schematic, the DNA template is depicted by a thick black line, the unphosphorylated form of the core pol II (IIA) by an open ellipsoid with its unphosphorylated CTD as a thin curved line, and the nine subunits TFIIH as striped forms with the CDK7 as a solid circle. Tat is designated as an open circle and the transcription initiation site with an arrowhead. Nascent RNA is designated by a line with a large dot at its 5' terminus, the CTD is depicted by a curved line with a partially thickened section, and the highly phosphorylated form of pot II (IIO) is depicted as a filled ellipsoid with its CTD as a thick curved line.

The human immunodeficiency virus (HIV) encodes the transcriptional trans-activator Tat, which functions to increase rates of elongation rather than initiation of transcription by RNA polymerase II from the HIV promoter. The present invention provides methods of inhibiting Tat trans-activation and methods of assaying for such inhibitors. The methods of the invention are thus useful for developing HIV therapeutics. In addition, because Tat trans-activation is mediated by a cyclin dependent kinase (CDK7), the methods of the invention are also useful for regulating the cell cycle and providing inhibitors for pathologically proliferating cells such as cancer cells.

The present invention is based on the discovery that Tat binds directly to the cyclin-dependent kinase 7 (CDK7), which leads to productive interactions between Tat and the CDK-activating kinase (CAK) complex and between Tat and TFIIH. Tat therefore activates the phosphorylation of the C-terminal domain (CTD) of pot II by CAK. The ability of CAK to phosphorylate the CTD can be specifically inhibited, e.g., by a CDK7 pseudosubstrate, which inhibits trans-activation by Tat. This inhibition is specific to Tat and does not result in toxic effects to the cell.

II. Definitions

As used herein, the following terms have the meanings ascribed to them unless specified otherwise.

The term "pseudosubstrate" refers to a molecule that binds to the active site of a catalytic polypeptide such as CDK7 and Tat. Pseudosubstrates can include molecules such as polypeptides, small chemical molecules, nucleotides and the like.

The term "pol II" refers to the mammalian RNA polymerase II holoenzyme transcription complex, including core pol II comprising a CTD (C-terminal domain) and the TFIIH subunit comprising CAK, which includes CDK7.

The term "inhibitor" refers to molecules that interfere with CDK7-mediated Tat trans-activation of HIV transcription. Such molecules can be identified using the assays described herein and can be molecules such as pseudosubstrates, small chemical molecules, nucleotides, antibodies, and the like. Assays for Tat activated trans-activation treated with a suspected inhibitor are compared to control samples without the inhibitor, to examine the extent of inhibition. Control samples (untreated with inhibitors) are assigned a relative Tat trans-activation value of 100. Inhibition of Tat trans-activation is achieved when the Tat trans-activation value relative to the control is about 75, preferably 50, more preferably 25.

III. HIV and Tat trans-activation

The lentiviruses human immunodeficiency virus (HIV) type 1 (HIV-1), and type 2 (HIV-2) cause the disease AIDS, and are epidemic in human populations world wide. HIV-1 and HIV-2 are genetically related, antigenically cross reactive, and share a common cellular receptor (CD4) (for an overview of HIV infection, see, e.g, *Fundamental Immunology* (Paul, ed. 1993)). HIV corrupts the cellular machinery of infected T cells by causing the cell to replicate copies of the HIV virus. Eventually HIV causes the death of infected immune cells, thereby disabling the immune system and killing the patient due to complications associated with a disabled immune system.

Due to the pandemic spread of HIV, an intense effort to unravel the molecular mechanisms and life cycle of these viruses is underway. The life cycle of these viruses provides many potential targets for inhibition, including inhibition of Tat, which is required for transcription of the HIV genome. Tat binds to the trans-activation response (TAR) RNA stem-loop in the viral long terminal repeat (LTR) and increases rates of elongation rather than initiation of transcription from the HIV promoter by RNA polymerase II (pol II). Tat also interacts with cellular proteins to increase rates of elongation by pol II.

The examples described herein indicate that Tat acts by binding directly to the cellular protein CDK7, and that this interaction mediates the association between Tat and CAK/TFIIH, a pol II subunit. Furthermore, Tat stimulates the ability of CAK and CAK/TFIIH complexes to phosphorylate the CTD of core pol II. Finally, whereas basal transcription from the HIV LTR promoter is independent of CDK7, the phosphorylation of the CTD by CDK7 is absolutely essential for Tat trans-activation of the HIV promoter and production of viral genomes and thus infectious virus particles.

A model is proposed for Tat trans-activation via CDK7 binding (FIG. 1). During assembly of the initiation complex, Tat, TFIIH and other components of the pol II holoenzyme (omitted for the sake of simplicity) associate with the core pol II onto the DNA template. Transcription initiates with the hydrolysis of ATP between the β and γ phosphates and the synthesis of the first phosphodiester bond. Tat enters into the transcription complex by virtue of its association with the pol II holoenzyme via CDK7 prior to docking of the complex onto the DNA template. After promoter clearance, pol II then copies promoter proximal sequences and TAR is synthesized. Following its interaction with TAR at the bulge region, Tat is re-positioned and/or modified such that it increases the ability of CDK7 to phosphorylate the CTD. Tat might function in a catalytic manner by modifying TFIIH, it may re-position TFIIH in closer proximity of the CTD, or it might increase the length of time that TFIIH remains in contact with the CTD. Upon phosphorylation, pol II is rendered highly processive and can now efficiently transcribe the entire viral genome.

VI. The role of CDK7 in cell cycle regulation

In association with cyclin H, CDK7 forms the CDK-activating complex (CAK), which phosphorylates cyclin dependent kinases as well as CTD. CDK7 itself is named "cyclin dependent kinase 7," on the basis of its association with cyclin H in the active phosphorylation trimer, CAK. Cyclins were originally identified by their accumulation and disappearance at defined points in the cell cycle (see, e.g., Arnold et al., *J. Clin. Invest.* 83:2034–2040 (1989); Murray & Kirschner, *Science* 246:614–621 (1989)). The cyclins are divided into several families based on functional and structural characteristics. Cyclins are involved in the regulation of the cell cycle and are expressed only a specific points in the cell cycle. The association of CDK7 with cell cycle specific proteins reveals that CDK7 and its inhibitors can also be used to regulate the cell cycle. Thus, modulation of CDK7 phosphorylation is important for treating diseases of pathologically proliferating cells, such as cancer, restenosis, hyperplasia and the like.

V. Mapping of Tat-CDK7 binding

The present invention identifies CDK7 as the cellular protein that binds Tat during Tat trans-activation. Identification of the regions required for Tat-CDK7 binding allows development of inhibitors of Tat trans-activation and therefore HIV therapeutics. The structure of the Tat-CDK7 complex can be analyzed using, for instance, NMR and x-ray crystallographic techniques. Examination of the crystal structure of the complex provides information on the precise regions on both Tat and CDK7 involved in binding. For a description of this approach to analyzing receptor-ligand interactions see, de Vos et al., *Science* 255:306–312 (1992). Knowledge obtained by these studies is particularly useful in rational drug design (see, e.g., Fuh et al., *Science* 256:1677–1680 (1992)).

Tat and CDK7 are useful in rational drug design for screening test compounds, e.g. peptides, small chmical molecules and the like, for the ability to inhibit binding between Tat and CDK7. Test compounds used in the assays of the present invention can be synthetic or naturally-produced biomolecules, such as a polypeptides, immunoglobulins, carbohydrates (e.g., oligosaccharides), glycoconjugates, nucleic acids, and the like. The amino acid and nucleotide sequences of Tat and CDK7 are known and can be used to identify amino acid subsequences that inhibit Tat-CDK7 complex formation (see, e.g., Cujec et al., *Mol. Cell. Biol.* 17:1817–1823 (1997); Fisher & Morgan, *Cell* 78:713–724 (1994)).

Binding between Tat and CDK7 can also be analyzed using standard recombinant nucleic acid techniques (see, e.g., Ausubel supra; Sambrook et al., supra). Both Tat and CDK7 mutants can be constructed, expressed, and used in vitro and in vivo assays to identify regions of the proteins involved in binding. For example, the Tat activation domain, which interacts with cellular transcriptional machinery (48 N-terminal amino acids), can be analyzed using linker-scanner mutants. Genes that express N- or C-terminally truncated Tat or CDK7 can also be constructed and assayed as described below for Tat trans-activation function. For example, nested deletion constructs can be made and tested to determine the minimum amino acid sequences required for Tat-CDK7 binding.

DNA sequences which encode a polypeptide (e.g., a portion of Tat or CDK7) may be cloned and expressed to provide the polypeptide. Cells that express Tat or CDK7 can be used as a source of the DNA sequences. Standard techniques can be used to screen cDNA libraries or amplify nucleic acids with primers to identify sequences encoding the desired sequences (see, e.g., Sambrook et al., *Molecular Cloning—A Laboratory Manual* (1989)). Recombinant Tat and recombinant CDK7 have been cloned and isolated (see, e.g., Cujec et al., *Mol. Cell. Biol.* 17:1817–1823 (1997); Fisher & Morgan, *Cell* 78:713–724 (1994)). The genes encoding Tat and CDK7 can be cloned into any suitable vector for introduction into cells and protein expression.

Recombinant Tat and CDK7 are conveniently isolated from the cells above using standard protein purification techniques. In addition, naturally occuring Tat and CDK7 can be isolated from cells for inhibition assays and binding assays. The protein can be purified by any of a variety of known techniques, including, for example, reverse phase high-performance liquid chromatography (HPLC), ion-exchange or immunoaffinity chromatography, separation by size, or electrophoresis (see, e.g., Scopes, *Protein Purification* (1982). The isolated proteins are then tested for binding and Tat trans-activation using any of the assays described below.

VI. Assays for inhibition of Tat trans-activation

The present invention demonstrates for the first time the specific cellular protein that binds to Tat (CDK7) during Tat trans-activation of HIV promoters. Thus, the interaction between Tat and CDK7 can be used to identify substances that inhibit Tat trans-activation. Inhibition of Tat trans-activation can occur at any point in the cascade of steps involved CDK7-catalyzed Tat trans-activation, from Tat binding to CDK7 to the phosphorylation of CTD. For example, Tat-CDK7 binding can be inhibited, CDK7 association with CAK can be inhibited, CAK association with TFIIH can be inhibited, etc. The inhibitors of the invention can include, e.g., pseudosubstrates, antibodies, small organic molecules, nucleotides, and other molecules that bind, interfere, or sequester or otherwise inhibit this cascade of interactions.

The ability of molecules to inhibit Tat trans-activation can be assessed using a variety of in vitro and in vivo assays. For example, Tat trans-activation can be assessed using in vitro run-off transcription reactions with transcription extracts (see, e.g., *Current Protocols in Molecular Biology* (Ausubel et al., eds., 1997)). In such an assay, nuclear transcription extracts are prepared from cultured mammalian cells according to standard procedures (see, e.g., Dignam et al., *Nuc. Acids. Res.* 11:1475–1489 (1983)). Recombinant Tat protein is isolated according to standard procedures and added to the nuclear transcription extract along with the other components of the transcription reaction such as nucleotides (see, e.g., Cujec et al., supra; Example V). The reaction is also supplied with HIV promoter DNA sequences operably linked to a structural gene.

Similarly, the assay may be performed in vitro. A suitable cultured mammalian cell lines such as COS or HeLa cells is transduced by standard methods with an DNA vector having an HIV promoter operably linked to a structural gene. The cells are cultured according to standard conditions (see, e.g., Freshney, *Culture of Animal Cells* (3d ed., 1994)). Approximately 24–48 hours post transduction, cells are harvested and examined for transcription from the HIV promoter.

Transcription of the structural gene operably linked to the HIV promoter can be detected in a number of ways. Radio-active nucleotides such as $\alpha$-[$^{32}$P]UTP can be added to an in vitro reaction and then the reaction products analyzed by gel electrophoresis. RNase protection assays or northern analysis can be used to analyze unlabeled transcripts, or reporter genes such as CAT can be transcribed and analyzed for reporter production.

In addition to trans-activation assays, phosphorylation of CTD can also be used as an assay to indirectly measure Tat trans-activation and inhibition. Typically, kinase reactions are performed in vitro. The substrate (in this case CTD) is immunoprecipitated from cells and incubated with Tat CDK7 (in the CAK complex) under standard reaction conditions including $\gamma$-[$^{32}$P]ATP (see, e.g., Example III). Phosphorylation of the substrate is examined using electrophoresis and changes in electrophoretic mobility.

Molecules that are potential inhibitors of Tat trans-activation include pseudosubstrates, small chemical molecules, nucleotides, peptides, antibodies, and the like. The inhibitor can be introduced to the cell by a variety of methods, including transfection, electroporation, infection, lipofection, passive diffusion, lipid solubility, and active transport.

Cell samples or assays that are treated with a potential Tat trans-activation inhibitor are compared to control samples without the inhibitor, to examine the extent of inhibition. Typically, an in vitro or in vivo Tat trans-activation assay is contacted with a potential inhibitor. In parallel with an untreated control assay (without the potential inhibitor), the assays are incubated for a suitable period of time, and then examined for Tat trans-activation. Control samples (untreated with inhibitors) are assigned a relative Tat trans-activation activity value of 100. Inhibition of Tat trans-activation is achieved when the Tat trans-activation activity value relative to the control is about 75, preferably 50, more preferably 25.

For example, one type of potential inhibitor is a pseudosubstrate molecule that binds to the active site of CDK7. A pseudosubstrate may be, e.g., a small chemical molecule or a peptide. One embodiment of a pseudosubstrate inhibitor of Tat trans-activation is the peptide mC2p, which corresponds to amino acids 149 to 170 of CDK (a natural substrate of CDK7). This peptide contains a T to A mutation that changes the codon for the threonine at amino acid 190, which is normally phosphorylated by CDK7.

Pseudosubstrate peptides can be made using any of a number of standard techniques. Conveniently, they can be synthesized by conventional techniques employing automatic synthesizers, such as the Beckman, Applied Biosystems, or other commonly available peptide synthesizers using well known protocols. They can also be synthesized manually using techniques well known in the art (see, e.g., Stewart & Young, *Solid Phase Peptide Synthesis* (2nd ed. 1984). "Peptide" and "polypeptide" refer to a polymer composed of amino acid residues, related naturally occurring structural variants, and synthetic non-naturally occurring analogs thereof linked via peptide bonds, related naturally occurring structural variants, and synthetic non-naturally occurring analogs thereof. The pseudosubstrates peptides of the invention can therefore be composed of naturally occurring amino acids as well as amino acid analogs.

VII. Administration of Tat trans-activation inhibitors

Inhibitors of Tat trans-activation can be administered directly to a patient, preferably a human. Administration is by any of the routes normally used for introducing a molecule into ultimate contact with blood or tissue cells. Tat trans-activation inhibitors are administered in any suitable manner, preferably with pharmaceutically acceptable carriers. Suitable methods of administering such inhibitors in the context of the present invention to a patient are known to those skilled in the art. Typically, the inhibitors are administered e.g., in liposomes or other carriers suitable for crossing the cell membrane and delivering the inhibitor to the cell.

Pharmaceutically acceptable excipients are determined in part by the particular composition being administered, as well as by the particular method used to administer the composition. Accordingly, there is a wide variety of suitable formulations of pharmaceutical compositions of the present invention. Formulations suitable for parenteral administration, such as, for example, intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous administration is the preferred method of administration.

The dose administered to a patient, in the context of the present invention should be sufficient to effect a beneficial therapeutic response in the patient over time. In determining the effective amount of the inhibitor to be administered in the treatment or prophylaxis of virally-mediated diseases such as AIDS, the physician evaluates circulating plasma levels, vector toxicities, progression of the disease, and the production of anti-vector antibodies. The dose will be determined by the efficacy of the particular inhibitor and the condition of the patient, as well as the body weight or surface area of the patient to be treated. The size of the dose also will be determined by the existence, nature, and extent of any adverse side-effects that accompany the administration of a particular inhibitor in a particular patient. Administration can be accomplished via single or divided doses. For a typical 70 kg patient, a dose equivalent to approximately 0.1 $\mu$g to 10 mg are administered.

EXAMPLES

The following examples are provided by way of illustration only and not by way of limitation. Those of skill in the art will readily recognize a variety of noncritical parameters that could be changed or modified to yield essentially similar results.

Example I: Tat Interacts with TFIIH in vitro

Tat interacts with the pol II holoenzyme, and TFIIH is present in the pol II holoenzyme, playing an essential role in the phosphorylation of the CTD (Cujec et al., *Mol. Cell. Biol.* 17:1817–1823 (1997); Ossipow et al., *Cell* 83:137–146 (1995); Maldonado et al., *Nature* (London) 381:86–89 (1996)). Tat was examined for association with TFIIH independently of the pol II holoenzyme. To determine if Tat interacts with TFIIH in vivo, HA-tagged wild-type and mutant Tat proteins were expressed in COS cells.

Methods: Immunoprecipitations

The constructs pCMV-TAT(Tat)HA and pCMV-TAT (C30G)HA containing wild-type or mutant Tat (C30G) fused to the influenza virus hemaglutinin (HA) epitope tag (3') were described previously (Cujec et al., *Mol. Cell. Biol.* 17:1817–1823 (1997)). A second HA-tagged mutant of Tat (K41A) was constructed by PCR-mediated mutagenesis. Briefly, PCR primers K41A (CATTGCTACGCGTGTTTCAC-AAGAgccGGCTTAGGC, lower case letters denote mutation) and TAT3 (CAG-TCTGAGTAGTTCGAAGAGTAG) were used to amplify a 112 bp fragment of Tat which was then cloned into the Afl III and Hind III sites of pCMV-TATHA. Both mutations (C30G, K41A) are in the activation domain of Tat and render Tat inactive without affecting its RNA-binding ability or protein expression levels (Kuppuswamy et al., *Nucl. Acids Res.* 17:3551–3561 (1989)). The Tat constructs (5 $\mu$g) were transfected into COS-7 cells by liptofectin (10 $\mu$l) according to the manufacture's recommendations (Gibco BRL, Gaithersburg, Md.). Approximately 36 hours after transfection the cells were lysed (50 mM HEPES-KOH (ph 7.8), 0.5 M NaCl, 1%-Triton X100, 10 mM EDTA, 5 mM dithiothreitol (DTT), 0.1 mM phenylmethylsulfonyl fluoride (PMSF), 20 $\mu$g/ml aprotinin, 10 $\mu$g/ml leupeptin), and the supenatants immunoprecipitated with the indicated antibodies. Immunoprecipitates bound to protein-A-Sepharose beads were washed three times in CAK binding buffer (lysis buffer +10% glycerol). Washed beads were subjected to gradient (5% to 15%) sodium dodecyl sulfate-polyacrylamide gel electrophoresis (SDS-PAGE), transferred to Immobilon-NC membranes (Millipore, Bedford, Mass.) and reacted with the indicated antibodies. The proteins were visualized by enhanced chemiluminescence detection (Amersham, Arlington Heights, Ill.). The anti-HA antibody was purchased from Boehringer-Mannheim (Indianapolis, Ind.), the CDK7 antibody from Santa Cruz Biotechnology (Santa Cruz, Calif.), and the cyclin H antibody from Upstate Biotechnology (Lake Placid, N.Y.). The CIITA antibody was from our laboratory (Steimle et al., *Cell* 75:135–146 (1993)).

Results

Immunoprecipitations were done with an antibody against ERCC3 ($\alpha$ERCC3), which is the largest subunit of TFIIH. Since TFIIH is part of the pol II holoenzyme, co-immunoprecipitations were done under stringent conditions (0.5 M NaCl and 1% Triton X-100), which were expected to dissociate TFIIH from the pol II holoenzyme. To confirm that only TFIIH, and not the entire pol II holoenzyme, was immunoprecipitated in these experiments, $\alpha$ERCC3 immunoprecipitates were also probed with antibodies against the largest subunit of the core pol II (RPB1). $\alpha$ERCC3 antibodies efficiently precipitated ERCC3 and CDK7 subunits of TFIIH, but failed to precipitate pol II. As a control, antibodies against the transcriptional activator CIITA (Steimle et al., *Cell* 75:135–146 (1993)) (C) failed to co-immunoprecipitate any of the transcription factors. To determine if Tat could bind to TFIIH in vitro, $\alpha$ERCC3 immunoprecipitates were probed with $\alpha$HA antibodies. Although equivalent amounts of wild-type (Tat) and mutant (C30G and K41A) Tat proteins were expressed in COS cells, only the wild-type Tat was co-immunoprecipitated by the $\alpha$ERCC3 antibodies. Again, antibodies against the transcriptional activator CIITA (C) failed to coimmunoprecipitate Tat. Similar results were obtained when using $\alpha$CDK7 antibodies. Together these results demonstrate that Tat can interact with TFIIH in the absence of both the pol II holoenzyme and TAR in vivo.

Example II: Tat Binds to CDK7 In Vitro.

Although interaction between Tat and purified TFIIH in vitro was detected (Parada et al., *Nature* (London) 384:375–378 (1996)), repeated previous attempts to detect specific interactions between Tat and ERCC3, ERCC2, or p62 subunits of TFIIH have been unsuccessful. Of these proteins, only p62 bound to Tat and all mutant Tat proteins. Therefore, Tat was tested to determine whether it could bind to recombinant CAK in vitro.

Methods: Purification of Recombinant CAK Trimer

Recombinant baculoviruses encoding human CDK7 (Fisher et al., *Cell* 78:713–724 (1994)), MAT1 (Fisher et al., *Cell* 83:47–57 (1995)), and an N-terminally 6-histidine tagged version of cyclin H (Kim et al., *Cell* 77:599–608 (1994)) were constructed as described. $4 \times 10^9$ Sf9 insect cells were co-infected with all three baculoviruses (multiplicity of infection for each virus: 5 pfu/cell), incubated 2 days at 28° C., and harvested by centrifugation. Cells were resuspended in 120 ml buffer A (20 mM Na phosphate, 25 mM NaCl, 1 mM PMSF, 1 μg/ml leupeptin, 2 μg/ml aprotinin, 1 mM DTT (pH 7.4). NaCl concentration was raised to 300 mM and the lysate was clarified by centrifugation and loaded over tandem 5-ml Pharmacia HiTrap Chelating columns loaded with $CoCl_2$ and preequilibrated with buffer B (300 mM NaCl, 20 mM Na phosphate, 10% glycerol (pH 7.2)). The column was washed with buffer B+1 mM DTT and eluted with a linear gradient of 0–200 mM imidazole in buffer B+1 mM DTT. Fractions containing the CAK trimer were pooled, diluted 4-fold in buffer C (20 mM Hepes-NaOH, 1 mM EDTA, 10% glycerol, 1 mM DTT (pH 7.4)), and loaded on a 5 ml Pharmacia HiTrap Q column pre-equilibrated with buffer C. The column was washed with buffer C and eluted with a linear gradient of 25–1000 mM NaCl in buffer C. Fractions containing the CAK trimer were pooled and subjected to gel filtration on a 125 ml Pharmacia Superdex 200 column pre-equilibrated in buffer C+150 mM NaCl. Peak fractions were concentrated by ion exchange on a 1 ml Pharmacia HiTrap Q column. The pure CAK trimer (2 mg/ml; over 99% homogeneous) was stored at −80° C.

Results

Recombinant wild type and mutant Tat proteins were attached to streptavidin agarose beads by virtue of streptavidin binding peptides at their 3' termini (Cujec et al., *Mol. Cell. Biol.* 17:1817–1823 (1997)). CDK7, cyclin H and MAT 1 were co-expressed in insect cells by baculovirus infection. Extracts were initially purified over a HiTrap Chelating column and then an anion exchange column (HiTrap Q). Relevant fractions were further purified by gel filtration and concentrated on a second HiTrap Q column. The resulting CAK preparations were >99% pure and were subsequently used for crystallization studies. CAK was incubated with streptavidin-agarose beads alone (C) or with streptavidin-agarose beads containing wild-type (Tat) or mutant (mtat=K41A) Tat proteins bound to them. After washing, the presence of CAK was monitored by Western blotting using αcyclin H antibodies. Wild-type Tat, but not mutant Tat bound to CAK very efficiently since at least half of the input CAK was retained on Tat beads. Western blotting with αCDK7 and αMAT1 antibodies revealed the presence of the other CAK subunits as well.

The ability of each of the individual CAK subunits to bind to Tat was next tested. CDK7, cyclin H and MAT 1 were labeled with $^{35}S$-methionine by in vitro translation and CAK dimers or trimers were allowed to form. Complexes were immunoprecipitated with αCDK7 antibodies bound to protein-A-Sepharose beads. Immunoprecipitated complexes were then incubated with γ-$^{32}$P-ATP labeled Tat and the ability of CDK7-beads to retain Tat was evaluated. Equal amounts of Tat were retained on these beads regardless of whether CDK7 was present alone, as a dimer with cyclin H, or as the CAK trimer. Although equivalent amounts of wild-type (T) or mutant (mT) Tat proteins were used in these experiments, the mutant Tat did not bind to any CDK7 complexes. As expected, addition of MAT 1 to the CDK7-cyclin H dimers stabilized the CAK complex (Fisher et al., *Cell* 83:47–57 (1995)) and increased the amount of CAK immunoprecipitated by αCDK7 antibodies.

These results suggest that the reticulocyte lysate contained minimal amounts of endogenous cyclin H or MAT 1 proteins, which could associate with the introduced CDK7 monomer or CDK7-cyclin H dimer and form the tripartite CAK complex. Similar experiments failed to reveal specific interactions between Tat and cyclin H or MAT 1 in the absence of CDK7. Together, these results demonstrate that Tat can interact with CDK7 directly and that this interaction leads to the association of Tat with the higher order CAK and TFIIH complexes.

Example III: Tat increases the Ability of CAK to Phosphorylate the CTD

Having demonstrated a strong affinity between Tat and CAK, now the ability of Tat to affect CAK phosphorylation of the CTD of pol II was tested.

Methods: In vitro binding assays

For the CAK binding assays, wild-type Tat (Tat) or mutant Tat (TatK41A; mTat) proteins containing at their 3' ends both a phosphorylation site for the cAMP-dependent heart muscle kinase and a streptavidin binding peptide, were expressed in bacteria and bound to streptavidin-agarose beads as described previously (Cujec et al., *Mol. Cell. Biol.* 17:1817–1823 (1997)). Equilibrated Tat streptavidin-agarose beads were incubated with 25 μg of nuclear extract or 50 ng of purified CAK as described above. Pelleted beads were washed four times in CAK binding buffer (see above), and processed as described in the immnunoprecipitation protocol. For the CDK7 binding assays, Tat was eluted from the streptavidin-agarose beads with 0.8 M NaCl and 2 mM biotin and dialyzed into buffer D (25 mM HEPES-KOH (pH 7.6), 0.1 M KCL, 20% glycerol, 10 mM DTT, 0.1 mM EDTA). Approximately, 50 ng of eluted Tat was labeled using 10 units of catalytic subunit of cAMP-dependent heart muscle kinase (Sigma P-2645) and 20 μCi of [γ-32p]ATP. Kinase reactions were performed in 50 μl of 0.1 M Tris pH 7.5, 5 mM DTT, 0.5 M NaCl, 60 mM $MgCl_2$. CDK7, cyclin H and MAT 1 proteins were labeled with L-[$^{35}$S]methionine (>1000 Ci/mmol; Amersham) and the Promega TNT protein expression system. CAK complexes were formed in hybridization buffer (20 mM HEPES-KOH (pH 7.6), 50 mM KCl, 10 mM DTT, 5 mM EDTA and 10% glycerol) for 1 h at 4° C. and then immunoprecipitated with αCDK7 antibodies attached to protein-A-Sepharose beads. After binding the beads were washed three times in the hybridization buffer and then two times in CAK binding buffer (see above). Labeled Tat (0.5 ng) was added to the CDK7 complexes and incubated for 1 h at 25° C. Beads were washed again with binding buffer and then with PBS prior to loading onto SDS-PAGE (5% to 20% gradient). After drying the gels were visualized by autoradiography.

Results

Wild-type or mutant CAK/TFIIH complexes were immunoprecipitated from lysates of cells, which stably expressed HA-tagged wild-type CDK7 or its kinase-deficient variant (D155A). Although this mutation (D155A) abolishes the kinase activity of CDK7 it does not affect its ability to bind to cyclin H and MAT 1. Immunoprecipitates were incubated for increasing lengths of time with recombinant CTD and wild-type or mutant Tat proteins. The phosphorylation of the CTD by casein kinase (CK) was used as a marker for the electrophoretic mobility of the CTD. Since casein kinase only phosphorylates the CTD at one site, only the hypophosphorylated form of the CTD is apparent. Wild type but not mutant (mTat) Tat proteins increased the ability of immunoprecipitated CAK/TFIIH complexes to phosphorylate the hypophosphorylated ($CTD_a$) and hyperphosphorylated ($CTD_o$) forms of the CTD. The effect of Tat was evident after 20 min and increased throughout the duration of the experiment.

Tat did not affect the ability of CAK/TFIIH complexes to auto-phosphorylate cyclin H. As a control for the specificity of the inmnunoprecipitations, kinase deficient CAK/TFIIH complexes (M) were also immunoprecipitated. As expected, these complexes failed to phosphorylate the CTD and cyclin H.

Since approximately 10% of CAK is part of TFIIH, and the rest exists as a free complex (Drapkin et al., Trends Biochem. Sci. 19:504–508 (1994); Fisher et al., Cell 78:713–724 (1994); Fisher et al., Cell 83:47–57 (1995)), immunoprecipitations with αCDK7 antibodies would be expected to yield both CAK and some TFIIH. To test directly whether Tat could affect the ability of CAK to phosphorylate the CTD, recombinant CAK was incubated with CTD in the presence or absence of wild-type or mutant Tat proteins. Wild-type Tat (Tat) was much more effective at stimulating the ability of CAK to phosphorylate the CTD than the mutant Tat protein (mTat). The wild-type Tat also increased the ability of CAK to phosphorylate highly purified preparations of pol II. In neither case did Tat affect the phosphorylation of cyclin H. The CDK7 monomer was incapable of phosphorylating the CTD. By demonstrating that Tat can increase the kinase activity of CDK7, we provide functional relevance for the binding results presented in the previous section.

To test for the specificity of these effects of Tat, Tat was examined to determine whether it affected the ability of CAK to phosphorylate cyclinAΔ171/CDK2-HA complexes. CycliaAΔ171/CDK2HA complexes were bound to protein-A-Sepharose beads and incubated with CAK in the presence of wild-type or mutant Tat proteins. Since the ability of cyclinAΔ171/CDK2HA to phosphorylate histone H1 is dependent upon the phosphorylation of CDK2 by CAK, the phosphorylation of histone H1 can be used as a measure of CAK activity (Fisher et al., Cell 78:713–724 (1994)). Neither the wild-type (Tat) nor mutant Tat (mTat) affected the ability of CAK to phosphorylate cyclinAΔ171/CDK2HA.

Example IV: A CDK2 Mutant Peptide Inhibits the Phosphorylation of the CTD by CAK The activity of some kinases can be inhibited by excess amounts of substrate peptides which contain a mutation in the amino acid phosphorylated by the kinase of interest (Poteet-Smith et al., J. Biol. Chem. 272:379–388 (1997)). Since CAK phosphorylates the threonine of CDK2 at position 160 (Fisher et al., Cell 78:713–724 (1994); Makela et al., Nature (London) 371:254–257 (1994)), a CDK2 peptide (amino acids 149 to 170) having a T→A mutation (mC2p) was tested to determine whether it could inhibit phosphorylation of the CTD by CAK.

Methods: Kinase Reactions

GST-CTD fusion proteins were expressed in E. coli using pGCTD (a generous gift of W. Dynan) as described (Peterson et al., Genes Dev. 6:426–438 (1992)). Fusion proteins were eluted from glutathione-Sepharose beads with 15 mM glutathione and purified by gel filtration on a S-300 column (Pharmacia, Piscataway N.J.). Approximately 25 ng of the eluted GST-CTD fusion was used in each kinase reaction. Purified preparations of pol II (a generous gift of C. Kane) were obtained as described (Hodo et al., Biochemistry 16:2334–2343 (1977); Kerppola et al., Biochemistry 29:269–278 (1990)) except that a Mono S column was used instead of a DEAE-5PW column in the final step of the purification. CAK/TFIIH complexes were immunoprecipitated from HeLa cells which stably expressed HA-tagged wild-type CDK7 or a kinase-deficient mutant (D155A) under the control of a tetracycline-repressable promoter. Cell were lysed (50 mM HEPES-KOH (pH 7.6), 150 mM NaCl, 5 mM EDTA, 0.1% Triton X-100, 5 mM DTT, 0.2 mM PMSF, 1 MM NaF, 0.1 mM NaVO$_4$, 10 μg/ml aprotinin, 1 μg/ml leupeptin) and immunoprecipitations done as described above. Typically wild-type CAK/TFIIH complexes were immunoprecipitated from four 150 mm culture dishes after four days of growth in the absence of tetracycline (10 μg/ml). Imnmunoprecipitated beads were washed three times with lysis buffer and then two times with CTD-kinase buffer (20 mM Tris (pH 7.6), 50 mM KC1, 5 mM MgCl$_2$, 2.5 mM MnCl$_2$, 10 mM DTT). Reactions were supplemented with 10 μCi of γ-ATP and 50 μM of unlabeled ATP in a final reaction volume of 50 μl. Reactions were incubated for 1 h at 30° C. In some experiments, recombinant CAK (50 ng) or casein kinase II (25 ng) (Upstate Biotechnology) was used as the source of kinase activity. Peptide concentrations were determined by the ESL Protein Assay (Boehringer-Mannheim) system. The sequences of mC2p and rC2p are ARAFGVPVRTYaHEVVTLWYRA (lower case letter denotes residue mutated from threonine), and HARTVGVWYRA-EYARFVTPaVV respectively. Histone H1 kinase assays were done as previously reported (Fisher et al. Cell 78:713–724 (1994)).

Results

Increasing amounts of the CDK2 mutant peptide (mC2p) were added to kinase reactions containing recombinant CAK (0.02 μM) in the presence or absence of Tat. A 65-fold molar excess of mC2p (1.3 μM) inhibited the kinase activity of CAK by 50%, while a 650-fold excess of the peptide (13 μM) abolished almost all the activity of CAK. Interestingly, mCp inhibited both Tat-dependent and Tat-independent activity of CAK, as well as the phosphorylation of cyclin H. A randomized peptide (rC2p) having the same net charge and solubility as mC2p had no effect on the kinase activity of CAK. The mutant peptide (mC2p) did not affect the ability of CDK8/cyclin C to phosphorylate the CTD, or the activity of cyclinAΔ171/CDK2HA.

Example V: The mutant peptide inhibits Tat Trans-activation in vitro.

Having demonstrated that Tat binds to CDK7, and that this interaction increases the ability of CAK to phosphorylate the CTD, the role of CAK in Tat trans-activation was examined.

Methods: In vitro transcription reactions

Run-off transcription reactions from the wild-type HIV LTR and AdMLT promoters linearized with NcoI and HindIII respectively, were carried out as described (Okamoto et al., Proc. Natl. Acad. Sci. USA 93:11575–11579 (1996); Cujec et al., Mol. Cell. Biol. 17:1817–1823 (1997)). Transcription reactions containing the DHFR promoter (500 ng) fused to a G-less cassette (linearized at Nco I) were supplemented with 3 mM (NH$_4$)$_2$SO$_4$, 2% PEG 8000, 50 units of T1 RNase (Boehringer-Mannheim), 500 U of RNase inhibitor (Boehringer-Mannheim) and contained 5 μM instead of 40 μM of unlabeled UTP. Phosphocreatine, poly (d)I-(d)C, and poly(rI-rC) were omitted from the reactions.

Results mC2p inhibition of CDK7-mediated kinase activity of CAK was used to examine the effect of this peptide on the function of Tat in vitro. The addition of recombinant Tat to transcription reactions containing the wild-type HIV LTR as the template stimulated transcription 10-fold compared to basal levels. Increasing concentrations of mC2p selectively inhibited Tat trans-activation. At a concentration of 65 μM, mC2p inhibited Tat trans-activation to basal levels, while at 130 μM, transcription was completely abolished. On the other hand, transcription in the absence of Tat was relatively unaffected by mC2p, even at high concentrations of the peptide (130 μM). As a control, the randomized rC2p peptide did not affect Tat trans-activation.

To control for the possibility that mC2p might affect other transcription factors nonspecifically, the effect of the peptide was tested on transcription from AdMLT and DHFR promoters. These promoters represent important controls since it has been demonstrated that transcription from the AdMLT promoter is independent of CDK7, while transcription from the DHFR promoter is absolutely dependent upon the kinase activity of CDK7 (Akoulitchev et al., Nature (London) 377:557–560 (1995)). Increasing concentrations of mC2p had no effect on the transcription from the AdMLT promoter. In contrast, mC2p inhibited the transcription from the DHFR promoter by more than 50% at a concentration of 65 μM and completely at a concentration of 130 μM. The randomized peptide had no effect on transcription from the DHFR promoter. These results, together with studies on the inhibition of the kinase activity, demonstrate that the phosphorylation of the CTD by CDK7 is required for Tat trans-activation in vitro.

Example VI: CDK7 is Required for Tat Trans-activation in vitro

To confirm that the kinase activity of CDK7 is required for Tat trans-activation in vivo, increasing amounts of mC2p were co-transfected into COS cells, in the presence or absence of Tat.

Methods: Electroporation and RNase Protection assays

For the peptide inhibition studies, $1 \times 10^7$ COS-7 cells were electroporated (500 μl) (BioRad, Hercules Calif.) at 210 v, 960 μF using 2 μg of reporter DNA (pHIVΔKBCAT) containing HIV-LTR sequences lacking NF-κB binding sites, 2 μg of effector DNA (pSVTAT or pSVTATZX) and varying concentrations of mC2p or rC2p, (1 μg/μl solution). For the CDK7 over-expression studies, COS-7 cells were transfected with lipofectin using 2 μg of reporter DNA (HIVSCAT and 4×Sp1), and 2 μg of effector DNA (pSVTAT or pSVTATZX) as described above. Vector alone or plasmids encoding HA-tagged wild type CDK7 (SRα-CDK7-HA) or mutant HA-tagged CDK7 (SRα—CDK7(D155A)-HA) were co-transfected as indicated. Cells were incubated in the OpμMEM medium for 5 h and harvested 48 h after transfection. Twenty micrograms of RNA were used for the RNase protection assays. To make the rabbit β-globin or the HIV LTR CAT probe, Sp6βTS or pPGEMI/WT vectors were linearized with Eco R1 and transcribed with Sp6 or T7 polymerases respectively to produce [α-32P] UTP-labeled RNA probes. Assays were performed as described (Okamoto et at., Proc. Natl. Acad. Sci. USA 93:11575–11579 (1996)), the protected fragments were separated on 11% polyacrylamide/urea sequencing gels and processed as outlined above.

Results

The reporter construct (pHIVΔKBCAT) consisted of the HIV LTR containing sequences encoding TAR, initiator sequences, the TATA box and three Sp1 binding sites. Since transcription from the FHV LTR can be activated through NF-κB binding sites during electroporation, the reporter construct lacked these sites (Tong-Starksen et al., Proc. Nat. Acad. Sci. USA 84:6845–6849 (1987)). Levels of specific transcripts were determined by the RNase protection assay. The production of long transcripts from the HIV LTR was dramatically reduced in the presence of low concentrations of mC2p (5 μM), and completely abolished at a peptide concentration of 10 μM. In contrast, production of short transcripts in the presence or absence of Tat was unaffected by mC2p, even at a peptide concentration of 20 μM. Although overall transcript levels appeared higher in the absence of the randomized peptide, the ratio of long to short transcripts remained the same regardless of peptide concentration. Similarly, increasing concentrations of rC2p had no effect on transcription in the absence of Tat (data not presented).

To examine further the role of CDK7 on the activity of Tat in vitro, wild-type or a kinase-deficient mutant (D155A) of CDK7 was overexpressed in COS cells. RNase protection assays were used to quantify levels of transcripts from the HIV LTR or from a promoter consisting of a TATA box and four Sp1 binding sites (4XSp1). Transfection of HA-tagged Tat dramatically increased the ratio of long transcripts (LT) to short transcripts (ST). As expected, Tat did not affect transcription from the 4XSp1 promoter. The co-transfection of the wild-type (WT) CDK7-HA construct resulted in significant increase in the ratio of long transcripts (LT) to short transcripts (ST) compared to cells expressing only the endogenous CDK7. In contrast, the co-transfection of the kinase-deficient mutant of CDK7 (Mut) inhibited the production of long transcripts to levels below those observed in cells expressing endogenous CDK7, but had relatively little effect on the production of short transcripts. The over-expression of wild-type or mutant CDK7 proteins had no effect on transcription from the 4XSp1 promoter, which was previously shown to be independent of the CTD (Gerber et al., Nature (London) 374:660–662 (1995)).

As additional controls, western blotting revealed that similar levels of Tat-HA and CDK-HA proteins were expressed in these experiments. Together with previous data, these results confirm that the transcriptional activation by Tat is dependent upon the kinase activity of CDK7.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of screening in vitro for inhibitors of Tat binding to CDK7, thereby inhibiting TAT-activated, CDK7-catalyzed phosphorylation of CTD, the method comprising the steps of:
   (a) contacting Tat, pol II, and HIV promoter sequences operably linked to a structural gene with a substance suspected of inhibiting Tat binding to CDK7; and
   (b) assaying for Tat trans-activation of the HIV promoter sequence operably linked to the structural gene.

2. The method of claim 1, wherein the assay is an in vitro run-off transcription assay.

3. The method of claim 1, wherein the assay is a cellular transcription assay.

4. The method of claim 1, wherein the inhibitor is a fragment of Tat.

5. The method of claim 1, wherein the inhibitor is a fragment of CDK7.

6. The method of claim 1, wherein the inhibitor is a CDK7 pseudosubstrate.

7. The method of claim 6, wherein the pseudosubstrate is a peptide.

8. The method of claim 1, wherein the inhibitor is a small chemical molecule.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 36 base pairs
      (B) TYPE: nucleic acid -continued

```
        (C) STRANDEDNESS: single
        (D) TOPOLOGY: linear (ii) MOLECULE TYPE: DNA (xi) SEQUENCE DESCRIPTION: SEQ ID NO:1:

CATTGCTACG CGTGTTTCAC AAGAGCCGGC TTAGGC                    36

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CAGTCTGAGT AGTTCGAAGA GTAG                                 24

(2) INFORMATION FOR SEQ ID NO:3:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Ala Arg Ala Phe Gly Val Pro Val Arg Thr Tyr Ala His Glu Val Val
1               5                   10                  15

Thr Leu Trp Tyr Arg Ala
            20

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

His Ala Arg Thr Val Gly Val Trp Tyr Arg Ala Glu Tyr Ala Arg Phe
1               5                   10                  15

Val Thr Pro Ala Val Val
            20
```